(12) United States Patent
Huang et al.

(10) Patent No.: US 9,897,608 B2
(45) Date of Patent: Feb. 20, 2018

(54) DETECTION OF OVARIAN CANCER USING ANTIBODY ARRAYS

(71) Applicants: Raybiotech,Inc. Guangzhou, Guangzhou (CN); South China Biochip Research Center in Guangzhou, Guangzhou (CN)

(72) Inventors: Ruopan Huang, Guangzhou (CN); Weidong Jiang, Alpharetta, GA (US); Ruochun Huang, Guangzhou (CN)

(73) Assignees: Raybiotech, Inc. Guangzhou (CN); SOUTH CHINA BIOCHIP RESEARCH CENTER IN GUANGZHOU (CN)

( * ) Notice: Subject to any disclaimer, the term of this patent is extended or adjusted under 35 U.S.C. 154(b) by 0 days.

(21) Appl. No.: 14/915,395

(22) PCT Filed: Jul. 22, 2014

(86) PCT No.: PCT/CN2014/082747
§ 371 (c)(1),
(2) Date: Feb. 29, 2016

(87) PCT Pub. No.: WO2015/027779
PCT Pub. Date: Mar. 5, 2015

(65) Prior Publication Data
US 2016/0216267 A1 Jul. 28, 2016

(30) Foreign Application Priority Data
Aug. 30, 2013 (CN) .......................... 2013 1 0389388

(51) Int. Cl.
G01N 33/53 (2006.01)
G01N 33/574 (2006.01)
G01N 33/577 (2006.01)

(52) U.S. Cl.
CPC . *G01N 33/57449* (2013.01); *G01N 33/57484* (2013.01); *G01N 2333/4706* (2013.01); *G01N 2333/4725* (2013.01); *G01N 2333/70578* (2013.01); *G01N 2333/71* (2013.01); *G01N 2333/8146* (2013.01); *G01N 2800/60* (2013.01)

(58) Field of Classification Search
None
See application file for complete search history.

(56) References Cited

U.S. PATENT DOCUMENTS

| 8,501,669 | B2 * | 8/2013 | Selinfreund | ....... | A61B 10/0045 435/325 |
| 2008/0064113 | A1 * | 3/2008 | Goix | .................. | C07K 16/2875 436/86 |
| 2012/0231963 | A1 * | 9/2012 | Huang | ............. | G01N 33/57484 506/9 |
| 2015/0010582 | A1 * | 1/2015 | McMullen | ....... | G01N 33/57407 424/174.1 |

FOREIGN PATENT DOCUMENTS

CN 101833001 A 9/2010

OTHER PUBLICATIONS

Jiang et al., Identification of five serum proteins markers for detection of ovarian cancer by antibody arrays. PLOS One 8, e76795, 2013.*
Longuespèe et al. Ovarian cancer molecular pathology, Cancer Metastasis Rev 31, 713-732, 2012.*
Liss et al. Tissue inhibitor of metalloproteinase-4 is elevated in early-stage breast cancers with accelerated progression and poor clinical course. Am. J. Pathol. 175, 940-946, 2009.*
Hepatocyte growth factor-like protein—NCBI site searched on Jun. 19, 2017.*
Jiang, W.D. et al. Identification of five serum protein markers for detection of ovarian cancer by antibody arrays PLOS ONE Oct. 8, 2013(Oct. 8, 2013) vol. 8 No. 10 pp. 1-10.
International Search Report and Written Opinion for Application No. PCT/CN2014/082747 dated Oct. 15, 2014.
Gentry-Maharaj A, Menon U. Screening for ovarian cancer in the general population. Best Pract Res ClinObstetGynaecol. 2012;26(2):243-256 PMID: 22182415.
Schwartz PE, Taylor, K.J., "Is early detection of ovarian cancer possible?", Ann Med., 1995;27:519-528.
Bandera et al. "New technologies for the identification of markers for early detection of ovarian cancer"CurrOpinObstet Gynecol., 2003;15:51-55.
Lowe et al., "Effects of personal characteristics on serum CA125, mesothelin, and HE4 levels in healthy postmenopausal women at high-risk for ovarian cancer", Cancer Epidemiol Biomarkers Prev., 2008;17:2480-2487.
Badgwell,D. and Bast,R.C., "Early detection of ovarian cancer", Dis Markers 2007;23:397-410.
Jacobs,I.J. and Menon,U., "Progress and challenges in screening for early detection of ovarian cancer", Mol Cell Proteomics, 2004;3, 355-366.
Gorelik et al., "Multiplexed immunobead-based cytokine profiling for early detection of ovarian cancer", Cancer Epidemiol Biomarkers Prev, 2005;14(4):981-987.
Huang et al., "A biotin label-based antibody array for high-content profiling of protein expression", Cancer Genomics Proteomics, 2010;7(3):129-141. PMID: 20551245.

(Continued)

*Primary Examiner* — Elly-Gerald Stoica
(74) *Attorney, Agent, or Firm* — Lerner, David, Littenberg, Krumholz & Mentlik, LLP (57) ABSTRACT

Disclosed are antibody arrays for the detection of cancer in a human or animal subject, comprising a solid support having disposed thereon in a predetermined spatial configuration, a panel of antibodies specific to biomarkers comprising CA-125, MSP-α, TIMP-4, PDGF-Rα and OPG, wherein the panel comprises a first antibody or fragment thereof that specifically binds CA-125, a second antibody or fragment thereof that specifically binds MSP-α, a third antibody or fragment thereof that specifically binds TIMP-4, a fourth antibody or fragment thereof that specifically binds PDGF-Rα, and a fifth antibody or fragment thereof that specifically binds OPG. Also disclosed are systems containing the arrays and methods of using the arrays to detect cancer such as ovarian cancer.

3 Claims, 7 Drawing Sheets

(56) References Cited

OTHER PUBLICATIONS

Mor et al., "Serum protein markers for early detection of ovarian cancer", Proc Natl Aced Sci U S A, 2005;102(21):7677-7682. PMID: 15890779.
Huang R. P. (2007) Expert Rev. Proteomics 4:299-308.
Huang et al., (2005) Expert Opin. Ther. Targets 9:601-615.
Hashimoto et al., (2006) Obesity 14:799-811.
Ray et al., (2007) Nat. Med. 13:1359-1362.
Turtinen et al., (2004) Antimicrob, Agents Chemother, 48:396-403.
De Ceuninck et al., (2004) Biochem. Biophys. Res. Commun. 323:960-969.
Sell et al., (2006) Endocrinology 147:2458-2467.
Haddad & Belosevic (2009) Mol. Immunol. 46:576-586.
Vargas et al., (2005) Ann. Neurol. 57:67-81.
Liu et al., (2006) Am. J. Nephrol. 26:483-490.
Fu et al., (2007) Can. J. Ophthalmol. 42:865-869.
Coppinger et al., (2007) Blood 109:4786-4792.
Simcock et al., (2007) Am. J. Respir. Crit. Care Med. 176:146-153.
Kim et al., (2009) Chest 135:295-302.
Matsunaga et al., (2006) J. Allergy Clin, Immunol, 118:84-90.
Sack et al., (2005) Invest. Ophthalmol. Vis. Sci. 46:1228-1238.
Kverka et al., (2007) Clin. Chem. 53:955-962.
Fujita et al., (2008) Prostate 68:872-882.
MacBeath et al., (1999) J. Am. Chem. Soc. 121:7967-7968.
Lam et al., (2002) Current Opin. Chemical Biol. 6:353-358.
Ripley et al., Expression of matrix metalloproteinase-26 and tissue inhibitors of metalloproteinase-3 and -4 in normal ovary and ovarian carcinoma, Int J Gynecol Cancer, 2006;16(5):1794-1800. PMID: 17009974.
Lane et al., "Osteoprotegerin (OPG) protects ovarian cancer cells fromTRAIL-induced apoptosis but does not contribute to malignant ascites-mediated attenuation of TRAIL-induced apoptosis", J Ovarian Res, 2012;5(1):34. PMID: 23153223.
Madsen et al., "Immunohistochemical expression of platelet-derived growth factor receptors in ovarian cancer patients with long-term follow-up", Patholog Res Int, 2012:851432. doi:10.1155/2012/851432. PMID: 23094199.
Welm et al., "The macrophage-stimulating protein pathway promotes metastasis in a mouse model for breast cancer and predicts poor prognosis in humans", Proc Natl Acad Sci U S A, 2007;104(18):7570-7575.PMID: 17456594.
Schweitzer et al., (2000) Proc. Natl. Acad. Sci. U.S.A. 97:10113-10119.
Horie et al., (1996) Int. J. Hematol. 63:303-309 (providing Abstract only).

\* cited by examiner

Representative results of 174-marker Cytokine Antibody Arrays

Human Cytokine Antibody Array 6     Human Cytokine Antibody Array 7     Human Cytokine Antibody Array 8

Figure 3a

Artificial neural network analysis of 174-marker antibody arrays in ovarian cancers and healthy controls

Figure 3b

Top 8 markers in Artificial neural network analysis of 174-marker antibody arrays in ovarian cancers and healthy controls

Figure 4

Hierarchical cluster analysis of 174-marker antibody arrays in ovarian cancers and healthy controls

Correlation analysis between ELISA and antibody array assay

Array

ELISA

DETECTION OF OVARIAN CANCER USING ANTIBODY ARRAYS

CROSS-REFERENCE TO RELATED APPLICATIONS

The present application is a national phase entry under 35 U.S.C. § 371 of International Application No. PCT/CN2014/082747 filed Jul. 22, 2014, published in English, which claims priority from Chinese Patent Application No. 201310389388.4, filed Aug. 30, 2013, all of which are incorporated herein by reference.

BACKGROUND OF THE INVENTION

Ovarian cancer represents the third most frequent cancer and is one of the leading causes of cancer death among females in the United States and Europe (Gentry-Maharaj A, Menon U. Screening for ovarian cancer in the general population. Best Pract Res Clin Obstet Gynaecol. 2012; 26(2):243-256 PMID: 22182415; Schwartz P E, Taylor, K. J. Is early detection of ovarian cancer possible? Ann Med. 1995; 27:519-528; Bandera C A, Ye B, Mok S C. New technologies for the identification of markers for early detection of ovarian cancer. Curr Opin Obstet Gynecol. 2003; 15:51-55.). Most symptoms of ovarian cancer are vague and similar to those often experienced with more common, non-life-threatening health conditions. These symptoms might include abdominal swelling or bloating, pelvic pain or discomfort, lower back pain, loss of appetite or feeling full quickly, persistent indigestion, gas or nausea and changes in bowel or bladder habits. As a result, almost 80% of ovarian cancer patients are diagnosed at later stages. Unfortunately, the 5-year survival rate for patients with clinically advanced ovarian cancer is only 15% to 20%, in striking contrast to over 90% of 5-year survival rate for patients with stage I disease.

Currently, carcinoma antigen (CA)-125 and imaging are the two most common approaches for ovarian cancer screening tests. However, this marker has not proven useful for screening or diagnostic purposes due to low specificity and/or sensitivity. For example, serum CA-125 has been shown to have a sensitivity of greater than 98% but a specificity of only 50-60% for early-stage disease (Lowe K A, Shah C, Wallace E, Anderson G, Paley P, McIntosh M, et al. Effects of personal characteristics on serum CA125, mesothelin, and HE4 levels in healthy postmenopausal women at high-risk for ovarian cancer. Cancer Epidemiol Biomarkers Prev. 2008; 17:2480-2487; Badgwell, D. and Bast, R. C., Early detection of ovarian cancer. Dis Markers 2007; 23:397-410; Jacobs, I. J. and Menon, U. Progress and challenges in screening for early detection of ovarian cancer. Mol Cell Proteomics. 2004; 3, 355-366).

Multiple reports have identified serum ovarian cancer biomarkers using multiplex antibody array technology (Gorelik E, Landsittel D P, Marrangoni A M, Modugno F, Velikokhatnaya L, Winans M T, et al. Multiplexed immunobead-based cytokine profiling for early detection of ovarian cancer. Cancer Epidemiol Biomarkers Prev. 2005; 14(4): 981-987; Mor G, Visintin I, Lai Y, Zhao H, Schwartz P, Rutherford T, et al. Serum protein markers for early detection of ovarian cancer. Proc Natl Acad Sci USA. 2005; 102(21):7677-7682; PMID: 15890779; Huang R, Jiang W, Yang J, Mao Y Q, Zhang Y, Yang W, et al. A biotin label-based antibody array for high-content profiling of protein expression. Cancer Genomics Proteomics. 2010; 7(3):129-141; PMID: 20551245.). One report identified a group of 6 serum protein markers, including IL-6, IL-8, epidermal growth factor (EGF), vascular endothelial growth factors (VEGF), monocyte chemoattractant protein-1 (MCP-1), and CA-125, which displayed significant difference in serum concentrations between ovarian cancer and control groups with 84% sensitivity at 95% specificity (Gorelik E, Landsittel D P, Marrangoni A M, Modugno F, Velikokhatnaya L, Winans M T, et al. Multiplexed immunobead-based cytokine profiling for early detection of ovarian cancer. Cancer Epidemiol Biomarkers Prev. 2005; 14(4): 981-987). Another report identified a panel of 6 biomarkers (CA-125, OPN, IGF-II, MIF, Leptin and Prolactin) with a sensitivity of 95.3% and a specificity of 99.4% for the detection of ovarian cancer (Mor G, Visintin I, Lai Y, Zhao H, Schwartz P, Rutherford T, et al. Serum protein markers for early detection of ovarian cancer. Proc Natl Acad Sci USA. 2005; 102(21):7677-7682. PMID: 15890779). A 6-marker panel of proteins (IL-2 receptor-$\alpha$, endothelin, osteprotegerin, vascular endothelial growth factor D (VEGF-D) and betacellulin (BTC)) was used to distinguish ovarian cancer patients from normal subjects (Huang R, Jiang W, Yang J, Mao Y Q, Zhang Y, Yang W, et al. A biotin, label-based antibody array for high-content profiling of protein expression. Cancer Genomics Proteomics. 2010; 7(3):129-141. PMID: 20551245.).

However, there remains an exigent need to discover and develop biomarkers for ovarian cancer screening and early detection.

BRIEF SUMMARY OF THE INVENTION

A first aspect of the present invention is directed to an antibody array for the detection of cancer in a human or animal subject, comprising a solid support having disposed thereon in a predetermined spatial configuration, a panel of antibodies specific to biomarkers comprising CA-125, macrophage-stimulating protein (MSP)-$\alpha$, tissue inhibitor of metalloproteinase (TIMP)-4, alpha-type platelet-derived growth factor (PDGF-R$\alpha$) and osteoprotegrin (OPG), wherein the panel comprises a first antibody or fragment thereof that specifically binds CA-125, a second antibody or fragment thereof that specifically binds MSP-$\alpha$, a third antibody or fragment thereof that specifically binds TIMP-4, a fourth antibody or fragment thereof that specifically binds PDGF-R$\alpha$, and a fifth antibody or fragment thereof that specifically binds OPG. In some embodiments, the antibodies are monoclonal antibodies. In some embodiments, the solid support comprises glass.

Another aspect of the present invention is directed to a system for the detection of cancer in a human or animal subject, comprising the antibody array and a detectable biotin-binding polypeptide. The system may further include a system to detect the biotin-binding polypeptide and/or a system for solubilizing peptides contained in a biosample obtained from a human or animal subject. In some embodiments, the system for solubilizing peptides comprises a system for lysing cells of the biosample. In some embodiments, the biotin-binding polypeptide is avidin or streptavidin, or a biotin-binding variant thereof, and wherein the biotin-binding polypeptide is conjugated to a detectable label. In some embodiments, the detectable label is a dye, a fluorescent moiety, or an enzyme.

Further aspects of the present invention are directed to uses of the antibody arrays and systems in methods to detect cancer in a human or animal subject.

In some embodiments, the method of detecting cancer in a human or animal subject comprises: (a) obtaining a biosample from a human or animal subject; (b) biotinylating the biomarkers present in the biosample, wherein the biomarkers include CA-125, MSP-α, TIMP-4, PDGF-Rα and OPG; (c) contacting the biosample of b) with the antibody array under conditions suitable to form antibody-biomarker complexes; (d) contacting the antibody array of c) with a biotin-binding polypeptide under conditions whereby the biotin-binding polypeptide specifically binds the biotin moiety conjugated to the biomarkers present in the biosample; and (e) detecting the biotin-binding polypeptide bound to the biotin conjugated to the biomarkers.

In other embodiments, the method of detecting cancer in a human or animal subject comprises: (a) obtaining a biosample from a human or animal subject; (b) contacting the biosample of a) with the antibody array, wherein the antibodies disposed on the solid support are capture antibodies, under conditions suitable to form capture antibody-biomarker complexes; (c) contacting the antibody array of b) with a first detectably labeled detection antibody or fragment thereof that specifically binds CA-125, a second detectably labeled detection antibody or fragment thereof that specifically binds MSP-α, a third detectably labeled detection antibody or fragment thereof that specifically binds TIMP-4, a fourth detectably labeled detection antibody or fragment thereof that specifically binds PDGF-Rα, and a fifth detectably labeled detection antibody or fragment thereof that specifically binds OPG under conditions suitable to form biomarker-detection antibody complexes; and (d) detecting the detectably labeled detection antibodies bound to the biomarkers.

In some embodiments, the antibody arrays, systems and methods are used to detect ovarian cancer. In some embodiments, the subject is human. In some embodiments, the biosample is serum.

As demonstrated in the working example, an inventive embodiment containing a panel of antibodies specific to the 5 biomarkers MSP-α, TIMP-4, PDGF-Rα, and OPG and CA-125 effectively detected ovarian cancer with high specificity (95%) and high sensitivity (100%), with AUC=0.98, in sharp contrast to the results using CA-125 alone, which had an AUC of 0.87.

DETAILED DESCRIPTION

The present disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Numerical data such as ratios, concentrations and amounts may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically and practically possible.

Embodiments of the present disclosure will employ, unless otherwise indicated, techniques of medicine, organic chemistry, biochemistry, molecular biology, pharmacology, and the like, which are within the skill of the art. Such techniques are known in the art.

Antibody arrays or microarrays have emerged as a practical, fast and cost-effective way to conduct multiplexed, quantitative, protein expression profiling, functional determination and biomarker discovery, using very small amounts of sample (Huang R. P. (2007) Expert Rev. Proteomics 4:299-308; Huang et al., (2005) Expert Opin. Ther. Targets 9:601-615). Antibody microarrays typically include different antibodies arrayed at high spatial density on a solid support. Each antibody captures its target protein from a sample (such as serum or cell lysate), and the captured proteins are subsequently detected and quantified. Among different approaches of protein detection using antibody arrays, sandwich-based antibody arrays are the most common. The suitability of sandwich-based antibody arrays to detect differential protein expression patterns using various sample types has been well documented, e.g., serum (Hashimoto et al., (2006) Obesity 14:799-811), plasma (Ray et al., (2007) Nat. Med. 13:1359-1362), cell-cultured media (Turtinen et al., (2004) Antimicrob. Agents Chemother. 48:396-403; De et al., (2004) Biochem. Biophys. Res. Commun. 323:960-969), cell co-cultures (Sell et al., (2006) Endocrinology 147:2458-2467), cell and tissue lysates (Haddad & Belosevic (2009) Mol. Immunol. 46:576-586; Vargas et al., (2005) Ann. Neurol. 57:67-81), cerebrospinal fluid (Vargas et al., (2005) Ann. Neurol. 57:67-81), urine (Liu et al., (2006) Am. J. Nephrol. 26:483-490) abscess fluid (Fu et al., (2007) Can. J. Ophthalmol. 42:865-869), platelet releasates (Coppinger et al., (2007) Blood 109:4786-4792), bronchoalveolar lavage (Simcock et al., (2007) Am. J. Respir. Crit. Care Med. 176:146-153), sputum (Kim et al., (2009) Chest 135:295-302), breath condensates (Matsunaga et al., (2006) J. Allergy Clin. Immunol. 118:84-90), saliva (De et al., (2004) Biochem. Biophys. Res. Commun. 323: 960-969), tears (Sack et al., (2005) Invest. Ophthalmol. Vis. Sci. 46:1228-1238), prostatic fluid (Kverka et al., (2007) Clin. Chem. 53:955-962), and milk and colostrum (Fujita et al., (2008) Prostate 68:872-882).

The terms "antibody array" and "antibody microarrays" are used herein interchangeably and refer to an ordered spatial arrangement or configuration of five or more antibodies, each having specificity for one of the five biomarkers, on a physical substrate or solid support. In some embodiments, the antibodies are arranged by rows and columns due to the relative simplicity in making and assessing such arrangements. The spatial arrangement can, however, be essentially any form selected by the user, and preferably but need not be, in a pattern. In some embodiments, the antibody array contains the five antibodies that bind the five protein biomarkers arrayed on a glass slide at high density.

Antibody arrays can be fabricated by the transfer of antibodies onto the solid surface in an organized high-density format followed by chemical immobilization. Representative techniques for fabrication of an array include photolithography, ink jet and contact printing, liquid dispensing and piezoelectrics. The patterns and dimensions of antibody arrays are to be determined by each specific application. The sizes of each antibody spot may be easily controlled by the users. Antibodies may be attached to various kinds of surfaces via diffusion, adsorption/absorption, or covalent cross-linking and affinity. Antibodies may be directly spotted onto a plain glass surface. To keep antibodies in a wet environment during the printing process, high percent glycerol (e.g., 30-40%) may be used in sample buffer and the spotting is carried out in a humidity-controlled environment.

The surface of a substrate may be modified to achieve better binding capacity. For example, the glass surface may be coated with a thin nitrocellulose membrane or poly-L-lysine such that antibodies can be passively adsorbed to the modified surface through non-specific interactions. Antibodies may be immobilized onto a support surface either by chemical ligation through a covalent bond or non-covalent binding. There are many known methods for covalently immobilizing antibodies onto a solid support. For example, MacBeath et al., (1999) J. Am. Chem. Soc. 121:7967-7968) use the Michael addition to link thiol-containing compounds to maleimide-derivatized glass slides to form a microarray of small molecules. See also, Lam & Renil (2002) Current Opin. Chemical Biol. 6:353-358.

The nature of the solid support is not critical—among the large number of solid-support materials known in the art for use in the production of antibody arrays, silica or glass is most often used because of its great chemical resistance against solvents, mechanical stability, low intrinsic fluorescence properties, and flexibility of being readily functionalized. Examples of other solid supports that may be suitable for use in the present invention include polypropylene, polystyrene, polyethylene, dextran, nylon, amylases, natural and modified celluloses, polyacrylamides, agaroses and magnetite.

The antibody arrays of the present invention may be used to diagnose or detect cancer in a human or animal subject or patient, or to monitor the progression of the cancer of the response of a human or animal subject or patient to a treatment regimen. The term "cancer" as used herein, shall be given its ordinary meaning, as a general term for diseases in which abnormal cells divide without control. In particular, cancer refers to angiogenesis related cancer. Cancer cells can invade nearby tissues and can spread through the bloodstream and lymphatic system to other parts of the body. There are several main types of cancer. For example, carcinoma refers to cancer that begins in the skin or in tissues that line or cover internal organs. Sarcoma refers to cancer that begins in bone, cartilage, fat, muscle, blood vessels, or other connective or supportive tissue. Leukemia refers to cancer that starts in blood-forming tissue such as the bone marrow, and causes large numbers of abnormal blood cells to be produced and enter the bloodstream. Lymphoma refers to cancer that begins in the cells of the immune system.

In some embodiments, the cancer that is being detected is ovarian cancer. Representative examples of other cancers that may be diagnosed or detected in accordance with the present invention include bladder cancer, breast cancer, colorectal cancer, endometrial cancer, head and neck cancer, leukemia, lung cancer (e.g., non-small-cell lung cancer and small-cell lung cancer), melanoma, ovarian cancer, prostate cancer, testicular cancer, uterine cancer, cervical cancer, thyroid cancer, gastric cancer, brain cancer (e.g., brain stem glioma, cerebellar astrocytoma, cerebral astrocytoma, glioblastoma, ependymoma and medulloblastoma), Ewing's sarcoma family of tumors, germ cell tumor, extracranial cancer, leukemia (e.g., acute lymphocytic leukemia, adult acute myeloid leukemia, hairy cell leukemia, chronic lymphocytic leukemia, chronic myeloid leukemia, acute lymphoblastic leukemia, and acute myeloid leukemia), liver cancer, neuroblastoma, brain tumors generally, lymphoma (e.g., primary central nervous system lymphoma, and Hodgkin's and non-Hodgkin's lymphoma), osteosarcoma, malignant fibrous histiocytoma of bone, retinoblastoma, rhabdomyosarcoma, soft tissue sarcomas generally, supratentorial primitive neuroectodermal and pineal tumors, visual pathway and hypothalamic glioma, Wilms' tumor, esophageal cancer, renal cancer, multiple myeloma, oral cancer, pancreatic cancer, and skin cancer, among others.

As used herein, the terms "subject" and "patient" are used interchangeably and include mammals (e.g., humans and non-humans). For veterinary applications, a wide variety of subjects may be suitable, e.g., livestock such as cattle, sheep, goats, cows, swine, and the like; poultry such as chickens, ducks, geese, turkeys, and the like; and domesticated animals, particularly pets such as dogs and cats. For diagnostic or research applications, a wide variety of mammals will be suitable subjects, including rodents (e.g., mice, rats, hamsters), rabbits, primates, and swine such as inbred pigs and the like.

The term "biomarker" as used herein refers to an antigen such as a peptide, polypeptide, protein (monomeric or multimeric) that may be found on the surface of a cancer cell, or is an intracellular component of a cancer cell, or a component or constituent of a biosample such as a biofluid, e.g., a soluble protein in a serum sample and which is a characteristic that is objectively measured and evaluated as an indicator of cancer. The presence of such a biomarker in a biosample isolated from a subject human or animal can indicate that the subject has cancer. A change in the expression of the biomarker may correlate with an increased risk of disease or progression, or be predictive of a response of a disease to a given treatment.

The antibody panel of the present invention contains a first antibody having specificity to CA-125, a second antibody having specificity to TIMP-4, a third antibody having specificity to osteoprotegrin (OPG), a fourth antibody having specificity to PDGF-Rα, and a fifth antibody having specificity to MSP (macrophage-stimulating protein).

The term "antibody" as used herein encompasses monoclonal, polyclonal antibodies, chimeric antibodies, human antibodies and humanized antibodies, and fragments thereof that have binding specificity for the biomarker, e.g., single chain fragments, and mutants thereof. Antibodies specific to these biomarkers may be derived from any source, including, but not limited to, murine spp., rat, rabbit, chicken, human, or any other origin.

Antibodies specific to CA-125, TIMP-4, osteoprotegrin (OPG), PDGF-Rα, and MSP (macrophage-stimulating protein), and techniques for their preparation, are known in the art and are commercially available. In the context of the present invention, minimum detection levels for each of the five biomarkers are typically 10,000 pg/ml (MSP), 100 pg/ml (OPG), 10 pg/ml (PDGF-Rα), 100 pg/ml (TIMP-4) and 35 IU/ml (CA-125).

TIMP-4 belongs to the matrix metalloproteinase (MMP) superfamily. MMPs are essential elements in extra-cellular matrix (ECM) degradation, including regulating the release of ECM-bound cytokines and growth factors, which leads to angiogenesis, cellular invasion and, eventually, cancer metastasis. These MMPs are tightly controlled and regulated by several tissue inhibitors of metalloproteinases (TIMPs). These TIMPs also play a critical role in tumorigenesis. It has been reported that TIMP-4 showed elevated expression in ovarian cancer tissues by IHC analysis, indicating its potential role in tumorigenesis of ovarian cancer (Ripley D, Tunuguntla R, Susi L, Chegini N. Expression of matrix metalloproteinase-26 and tissue inhibitors of metalloproteinase-3 and -4 in normal ovary and ovarian carcinoma. Int. J. Gynecol. Cancer 2006; 16(5):1794-1800. PMID: 17009974).

Osteoprotegrin (OPG) belongs to the TNF superfamily. OPG can be linked to the nuclear factor kappa-light-chain enhancer of activated B cells (NFκB) and tumor necrosis factor-related apoptosis inducing ligand (TRAIL) signaling pathway to regulate the homeostasis of bone remodeling and to serve as a survival factor. It has been reported that OPG can serve as such survival factor by protecting TRAIL-induced apoptosis in ovarian cancer cells, indicating its potential role in the development and progression of ovarian cancer origin (Lane D, Matte I, Rancourt C, Piché A. Osteoprotegerin (OPG) protects ovarian cancer cells from TRAIL-induced apoptosis but does not contribute to malignant ascites-mediated attenuation of TRAIL-induced apoptosis. J Ovarian Res. 2012; 5(1):34. PMID: 23153223).

PDGF-Rα belongs to the PDGF superfamily. Serving as angiogenetic growth factors, PDGFs play an important role in cell growth, chemotaxis, angiogenesis and reconstruction of tumor stroma. PDGF-Rα is a receptor for PDGF family, which is important for tumor stroma reconstruction. It has been reported that PDGF-Rα showed higher expression in ovarian cancer tissues in comparison with adjacent normal tissues. It has also been reported that PDGF-Rα expressed more often in serous carcinomas than in endometriod and mucinous tumors (Madsen C V, Dahl Steffensen K, Waldstrøm M, Jakobsen A. Immunohistochemical expression of platelet-derived growth factor receptors in ovarian cancer patients with long-term follow-up. Patholog. Res. Int. 2012: 851432. doi:10.1155/2012/851432. PMID: 23094199.).

MSP (macrophage-stimulating protein) is a growth factor involved in activating macrophage stimulating receptor-1 (MSTR1). The α-chain of MSP (MSP-alpha) is secreted by cleavage of pro-MSP. There are reports showing that the MSP pathway plays an important role in tumor metastasis (Welm A L, Sneddon J B, Taylor C, Nuyten D S, van de Vijver M J, Hasegawa B H, et al. The macrophage-stimulating protein pathway promotes metastasis in a mouse model for breast cancer and predicts poor prognosis in humans. Proc. Natl. Acad. Sci. U.S.A. 2007; 104(18):7570-7575.PMID: 17456594).

Depending upon the type of cancer being detected, an antibody specific to a further biomarker may be included in the antibody array. Representative examples of biomarkers include activin A; IL-18 BPa, adiponectin/acrp30, IL-18 receptor-α/IL-1 R5, AgRP, IL-18 receptor 13/AcPL, ALCAM, IL-2 receptor-α, angiogenin, IL-2 receptor-α, AR (amphiregulin), IL-3, Axl, IL-4, B7-1/CD80, I-TAC/CXCL11, BCMA/TNFRSF17, leptin (OB), BDNF, LIF, β-NGF, LIGHT/TNFSF14, BLC/BCA-1/CXCL13, LIGHT/TNFSF14, BMP-5, MCP-2, BTC, MCP-3, cardiotrophin-1/CT-1, MCP-4/CCL13, CTLA-4/CD152, M-CSF, CXCL16, MMP-10, Dtk, MMP-13, EGF, MMP-9, EGF receptor/ErbB1, MSP-α-chain, endoglin/CD105, MSP β-chain, eotaxin/CCL11, NAP-2, eotaxin-2/MPIF-2, NGF R, eotaxin-3/CCL26, NT-4, ErbB3, OSM, Fas/TNFRSF6, Fas Ligand, PDGF receptor-β, FGF Basic, PDGF-AA, FGF-4, PDGF-AB, FGF-6, PDGF-BB, FGF-7/KGF, PIGF, FGF-9, P-selectin, follistatin, RAGE, GITR/TNFRF18, RANTES, HB-EGF, SCF, HCC-4/CCL16, SCF receptor/CD117, HGF, sgp130, I-309, Siglec-9, IGFBP-1, siglec-5/CD170, IGFBP-2, Tarc, IGFBP-3, TGF-α, IGF-I, TNF RI/TNFRSF1A, IGF-I, TNF R11/TNFRSF1B, IGF-I S receptor, TNF-β, IGF-II, TRAIL R1/DR4/TNFRSF 10/, IGF-II, TRAIL R3/TNFRSF 10C, IL-1α, TRAIL R4/TNFRSF 10D, IL-1β, TRANCE, IL-1 R4/ST2, TREM-1, IL-1 sRI, TROP/

TNFRSF19, IL-1 sRI, uPAR, IL-10, VCAM-1 (CD106), IL-10 receptor-β, VE-cadherin, IL-13 receptor-α1, VEGF, IL-13 receptor-α2, VEGF R2 (KDR), IL-17, VEGF R3, and any combination of two or more thereof.

As used herein, "biosample" and "sample" are used interchangeably and embrace both fluids (also referred to herein as fluid samples and biofluids) and tissue obtained from the subject. The term "biofluid" as used herein refers to a biological fluid sample such as blood samples, cerebral spinal fluid (CSF), urine and other liquids obtained from the subject, or a solubilized preparation of such fluids wherein the cell components have been lysed to release intra-cellular contents into a buffer or other liquid medium. The definition also includes samples that have been manipulated in any way after their procurement, such as by treatment with reagents, or enrichment for certain components, such as proteins or polynucleotides. The term "blood sample" embraces whole blood, plasma, and serum. Solid tissue samples include biopsy specimens and tissue cultures or cells derived therefrom, and the progeny thereof. A sample may comprise a single cell or more than a single cell. The biosample may also be a cultured population of cells derived from the subject human or animal. However, whenever the biosample comprises a population of cells, the method will first require that the constituents of the cells be solubilized by lysing the cells, and removing solid cell debris, thereby providing a solution of the biomarkers. Samples can be prepared by methods known in the art such as lysing, fractionation, purification, including affinity purification, FACS, laser capture micro-dissection or iospycnic centrifugation.

In some embodiments, an ELISA (also known as an antibody sandwich assay) may be performed following standard techniques as follows. Antibodies used as the capture antibodies for each of the five biomarkers are disposed on (e.g., coated onto) a solid support, which may then be washed at least once (e.g., with water and/or a buffer such as PBS-t), followed by a standard blocking buffer, and then at least one more wash. The solid support may then be brought into contact with the sample/biosample under conditions to allow antibody-biomarker complexes to form (e.g., incubating from 1 hour to about 24 hours at a temperature from about 4° C. to about room temperature). The support may then be washed at least once (e.g., with a buffer such as PBS-t). To detect the complexation between the capture antibodies and the biomarkers that may be present in the sample, secondary or "detection" antibodies are applied to the solid support (e.g., diluted in blocking buffer) under conditions to allow complexation between the secondary antibodies and the respective biomarkers (e.g., at room temperature for at least one hour). The secondary antibodies are selected so as to bind a different epitope on the biomarker than the capture antibody. The optimum concentrations of capture and detection antibodies are determined using standard techniques such as the "criss-cross" method of dilutions.

The detection antibody may be conjugated, directly or indirectly, to a detectable label. The term "detectable label" as used herein refers to labeling moieties known in the art. Said moiety may be for example, a radiolabel (e.g., $^3H$, $^{125}I$, $^{35}S$, $^{14}C$, $^{32}P$, etc.), detectable enzyme (e.g., horse radish peroxidase (HRP), alkaline phosphatase etc.), a dye (e.g., a fluorescent dye), a colorimetric label such as colloidal gold or colored glass or plastic (e.g., polystyrene, polypropylene, latex, etc.), beads, or any other moiety capable of generating a detectable signal such as a colorimetric, fluorescent, chemiluminescent or electrochemiluminescent (ECL) signal.

The term "dye" as used herein refers to any reporter group whose presence can be detected by its light absorbing or light emitting properties. For example, Cy5 is a reactive water-soluble fluorescent dye of the cyanine dye family. Cy5 is fluorescent in the red region (about 650 to about 670 nm). It may be synthesized with reactive groups on either one or both of the nitrogen side chains so that they can be chemically linked to either nucleic acids or protein molecules. Labeling is done for visualization and quantification purposes. Cy5 is excited maximally at about 649 nm and emits maximally at about 670 nm, in the far red part of the spectrum; quantum yield is 0.28 (FW=792). Suitable fluorophores (chromes) for the probes of the disclosure may be selected from, but not intended to be limited to, fluorescein isothiocyanate (FITC, green), cyanine dyes Cy2, Cy3, Cy3.5, Cy5, Cy5.5 Cy7, Cy7.5 (ranging from green to near-infrared), Texas Red, and the like. Derivatives of these dyes for use in the embodiments of the disclosure may be, but are not limited to, Cy dyes (Amersham Bioscience), Alexa Fluors (Molecular Probes Inc.), HILYTE™ Fluors (AnaSpec), and DYLITE™ Fluors (Pierce, Inc).

In some embodiments, the detectable label is a chromogenic label such as biotin, in which case the detection antibody-biotin conjugate is detected using Strepavidin/Horseradish Peroxidase (HRP) or the equivalent. The strepavidin may be diluted in an appropriate block and incubated for 30 minutes at room temperature. Other detectable labels suitable for use in the present invention include fluorescent labels and chemiluminescent labels.

The support may then be washed and the label (e.g., HRP enzymatic conjugate on the strepavidin) is detected using the following standard protocols such as a chromogenic system (the SIGMA FAST™ OPD system), a fluorescent system or a chemiluminescent system. The amounts of each of the biomarkers present in the sample may then be read on an ELISA plate reader (e.g., SpectraMax 384 or the equivalent). The concentration of each of the biomarkers may then be back-calculated (e.g., by using the standard curve generated from purified biomarker and multiplied by the dilution factor following standard curve fitting methods), and then compared to a control (generated from tissue samples obtained from healthy subjects).

In some embodiments, a single antibody for each of the five biomarkers may be used. In one such embodiment, a biosample, e.g., a biofluid, is contacted with a system of reagents, well-known in the art, that can attach biotin moieties to some or all of the constituent components of the sample, and especially to the protein or peptide constituents thereof, including the biomarkers. Following this biotinylation step, the biotinylated biosample may then be contacted with the antibody array that contains an array of antibodies specific to each of the biomarkers.

After an adequate incubation period, readily selected to allow the binding of any biomarker in the sample to its corresponding antibody of the array, the fluid sample is washed from the array. The array is then contacted with a biotin-binding polypeptide such as avidin or streptavidin, that has been conjugated with a detectable label (as described above in connection with the ELISA). Detection of the label on the array (relative to a control) will indicate which of the biomarkers captured by the respective antibody is present in the sample.

Regardless of the specific assay format, the biotin-label-based array methods are relatively advantageous from several standpoints. Biotin-label can be used as signal amplification. Biotin is the most common method for labeling protein and the label process can be highly efficient. Furthermore, biotin can be detected using fluorescence-streptavidin and, therefore, visualized via laser scanner, or HRP-streptavidin using chemiluminescence. Using biotin-label-based antibody arrays, most targeted proteins can be detected at pg/ml levels. The detection sensitivity of the present methods can be further enhanced by using 3-DNA detection technology or rolling circle amplification (Schweitzer et al., (2000) Proc. Natl. Acad. Sci. U.S.A. 97:10113-10119; Horie et al., (1996) Int. J. Hematol. 63:303-309).

The present invention will now be described in terms of the following non-limiting example.

EXAMPLES

Methodology/Principal Findings: Using a case-control study design of 34 ovarian cancer patients and 53 age-matched healthy controls, the expression levels of 174 proteins using antibody array technology were profiled and the CA125 level was determined using ELISA. The expression levels of those proteins were analyzed using 3 discriminant methods, including artificial neural network, classification tree and split point score analysis. A panel of 5 serum protein markers MSP-α, TIMP-4, PDGF-Rα, and OPG and CA125 effectively detected ovarian cancer with high specificity (95%) and high sensitivity (100%), with AUC=0.98, while CA125 alone had an AUC of 0.87.

MATERIALS AND METHODS

Ethical Statement

Written consent was obtained when collecting samples from both patients and healthy controls.

Sample Collection

The serum samples from 34 patients diagnosed with early-stage (I and II) or late-stage (III and IV) ovarian cancers and 53 age-matched healthy controls were collected and included in the study from the affiliated hospital, Sun Yat-sen University. Briefly, about 2 ml of venous blood was drawn from patients. Serum was collected and stored at −80° C. until needed. Information about ovarian cancer diagnosis, staging, histology, grade and age was made available. The identity of patients such as name, address, day of birth was not provided. All serum samples were aliquoted and stored at −80° C. until needed.

Antibody Array Technology

Semi-quantitative sandwich-based antibody arrays were developed with the panel of 174 serum markers. A pair of antibodies was used to detect each analyte. Capture antibodies were printed onto the glass slide matrixes. Serum samples were incubated with antibody chips. Following extensive washing to remove unspecific binding, a cocktail of biotinylated antibodies was added to the arrays. After extensive washing, the array slides were incubated with a horseradish peroxidase (HRP)-conjugated streptavidin. The signals were then visualized using a fluorescence scanner system. To increase the accuracy, two replicates per antibody were spotted and the averages of the signal intensities for both spots were used for all calculations. A coefficient of variation (CV) of about 10% was attained. The antibodies specific to CA-125, TIMP-4, OPG, PDGF-Rα, and MSP used to detect ovarian cancer are listed in Table 1.

TABLE 1

| | Capture Antibody | Vendor | Detetion Antibody | Vendor | Antigen | Vendor |
|---|---|---|---|---|---|---|
| MSP Chain | MAB352 | R&D | BAM3521 | R&D | 352-MS-050/CF | R&D |
| TIMP-4 | 119-16174 | RayBiotech | BAF974 | R&D | 230-00269 | Raybiotech |
| PDGF R alpha | 119-11860 | RayBiotech | BAF322 | R&D | 322-PR-050/CF | R&D |
| Osteoprotegerin/OPG | 119-12729 | RayBiotech | BAF805 | R&D | 805-OS/CF | R&D |
| CA125 | M86306M | Meridian | M86924M | Meridian | A43350H | Meridian |

ELISA Analysis

ELISA was performed according to the RayBio® ELISA manual (RayBiotech, Inc., Norcross, Ga., USA). Pre-coated 96-well ELISA plates with different capture antibodies were first blocked using a blocking buffer. Aliquots of diluted sera and serial concentrations of standard protein were loaded onto the ELISA plate in duplicate with 100 µl per well. The plates were incubated for 2 h at room temperature. Unbound materials were washed out, and biotinylated anti-cytokine detection antibody was added to each well. The plates were incubated for 1 h at room temperature. After washing, 100 µl of streptavidin-HRP conjugated antibodies were added to the wells and incubation was continued for an additional 30 minutes at room temperature. After extensive washing, color development was performed by incubation with substrate solution in the kits. After adding stop solution, the optical density (O.D.) at 450 nm was determined for each well by a microplate reader and the concentrations of the samples were determined by comparison to the standard concentration curves.

Data Analysis

An adjusted t-test was used to test the significance between ovarian cancer and healthy control samples. P value less than 0.05 was considered to be statistically significant.

To determine the signal threshold, signals from the arrays were measured in the absence of samples (using blocking buffer as a blank) and repeated 10 times. The signals generated using blanks were averaged and the standard deviation (SD) was calculated. Signals with values lower than the average blank signal +2×SD was considered as background.

The data were also analyzed using a neural network which facilitates the identification of the common protein expression profiles in order to predict cancer. For purposes of clinical studies, use of 80% of samples as a training set and 20% of samples as a test set will provide even greater accuracy in the success of prediction over time, as more data become available.

The data were also analyzed by split-point score analysis. The split point divides the sample space into two intervals, one for ovarian cancer and one for normal controls. The best split-point score of each marker was chosen to ensure the minimization of misclassified samples. A score of 0 was assigned to a sample if it fell in the normal control interval; a score of 1 was assigned to a sample if it fell in the ovarian cancer interval. Overall, an individual was assigned a score as the sum of these assigned scores from N different markers. Therefore, the range of such score was between 0 to N. A given threshold T was chosen to optimally separate ovarian cancer from healthy controls, i.e., a given individual with a total score of <T is predicted to have normal status, whereas an individual with a total score of >T was diagnosed as ovarian cancer.

From the above data, the specificity, sensitivity, PPV (positive predictive value), NPV (net predictive value), and ROC (receiver operating characteristic) were determined.

Figure 1:
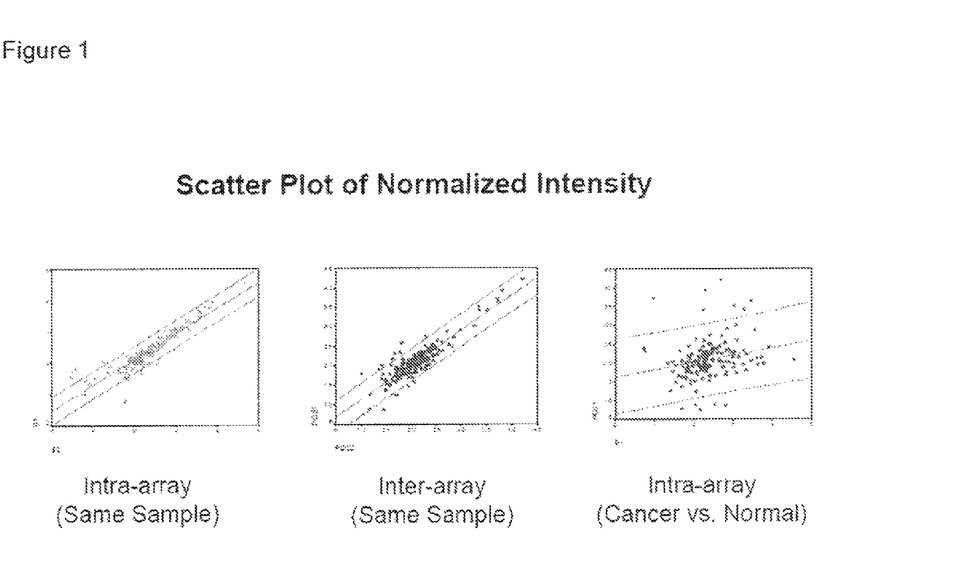
FIG. 1 shows a scatter plot for normalized intensity in 174-marker antibody arrays; Panel A (left) shows the strong correlation in the same sample assayed on the same log of membranes at the same day; Panel B (middle) shows the strong correlation in the same sample assayed on different logs of membranes at different days; and Panel C (right) shows the poor correlation between cancer and normal samples assayed on the same log of membranes at the same day.
Figure 2:
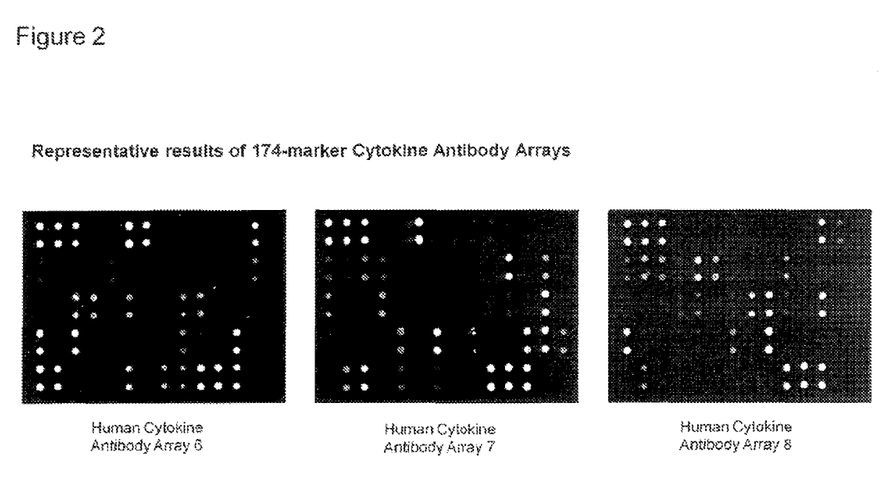
FIG. 2 shows representative results for 174-marker antibody arrays, wherein the representative result for array panel 6 is shown in Panel A (left); the representative result for array panel 7 is shown in Panel B (middle); and the representative result for array panel 6 is shown in Panel C (right).

Validation of 174-Marker Semi-Quantitative Cytokine Array (FIGS. 1, 2)

In this study, we applied antibody array technology to determine the expression profiles of 174 cytokines in the serum from ovarian cancer patients and age-matched healthy normal controls. Cytokines in this study included anti-inflammatory cytokines, proinflammatory cytokines, growth factors, angiogenic factors or chemotactic cytokines, among others. Some of these cytokines reportedly are altered in ovarian cancer patients from our own studies and literature, but our broad screen of 174 proteins also included many other types of markers as part of an unbiased approach of using high-content, high-throughput cytokine antibody arrays to profile the cytokine levels from ovarian cancer patients' serum with the goal for identification of potential diagnostic biomarkers.

First, we further determined the reproducibility of the assay in the analysis of human serum using scatter-plot analysis. Two types of experiments were performed. One is intra-array, in which two different sets of arrays were incubated with aliquots of the same sample, and the assay was performed at same time. The other is inter-array, in which two different sets of array membranes were assayed using the same sample at two different days. The Pearson correlation coefficients for intra-slides and inter-slides were 0.923 ($P<0.001$) and 0.899 ($P<0.001$) respectively, suggesting high reproducibility of the assay. In contrast, the Pearson correlation coefficient for cancer vs. normal samples were 0.226 ($P<0.005$), suggesting that the cancer samples and normal samples are from two different populations.

Next, serum samples from a total of 34 ovarian cancer patients and 53 healthy controls were assayed for expression levels of 174 cytokines with the goal of discovering new diagnostic markers for ovarian cancer. As shown in Table 2, these serum samples were mainly obtained from collaborators and were age- and sex-matched

TABLE 2

Study population characteristics.

| | Ovarian Cancer | Healthy Control |
|---|---|---|
| Total Number | 34 | 53 |
| Mean Age | 61.7 | 51.2 |
| Median Age | 66 | 56.2 |
| Age Range | 26-79 | 28-79 |
| Cancer Characteristics | | |
| Histology | | |
| Serous Adenoocarcinoma | 29 | |
| Mucious Adenocarcinoma | 4 | |
| Germline tumor | 1 | |
| Stage | | |
| Stage I | 4 | |
| Stage II | 3 | |
| Stage III & IV | 25 | |
| NA | 2 | |

Human Cytokine Antibody Arrays were used to profile expression patterns for 174 cytokines in all 87 patients' serum samples. The signal intensity was proportional to the expression level of an individual protein in each sample. To confirm the data, we performed ELISA assay to quantitatively measure the expression levels of these cytokines. The results were compared with the array data. The relative expression levels were similar between arrays and ELISA (see FIG. 6).

The array data were then normalized based on the positive control signal in each array. The signal intensities in every spot were then subtracted with individual background. The background level was determined by $+/-2SD$ of 10 control signal intensities, where the slides were assayed with blocking buffer only (i.e., without patient's serum samples). The values larger than backgrounds were considered as real signals (i.e., a positive detection of the cytokine). The values lower than backgrounds were considered as 1. If measured signal intensity values from all samples for a particular cytokine were 1, those cytokines were removed from the list for further analysis.

Identification of Serum Protein Markers by Artificial Neural Network Analysis

Figure 3A:
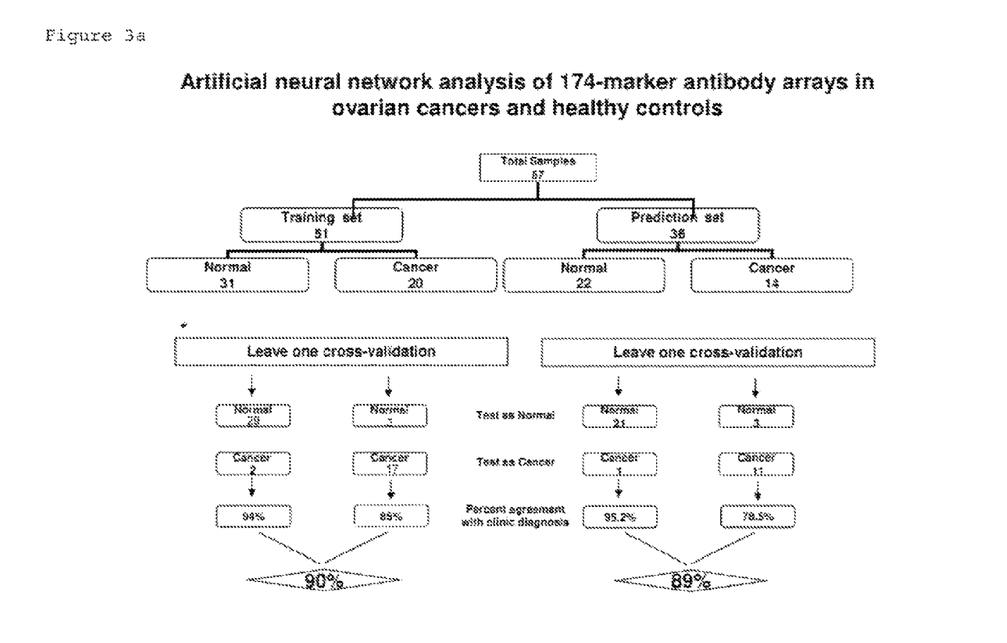
FIGS. 3A and B show an artificial neural network analysis of 174-marker antibody arrays in ovarian cancers and healthy controls, wherein 3A shows an artificial neural network analysis of 174-marker antibody arrays in ovarian cancers and healthy controls, including both training set and prediction set; and 3B shows top 8 markers with the greatest impact in artificial neural network analysis of 174-marker antibody arrays in ovarian cancers and healthy controls.
Figure 3B:
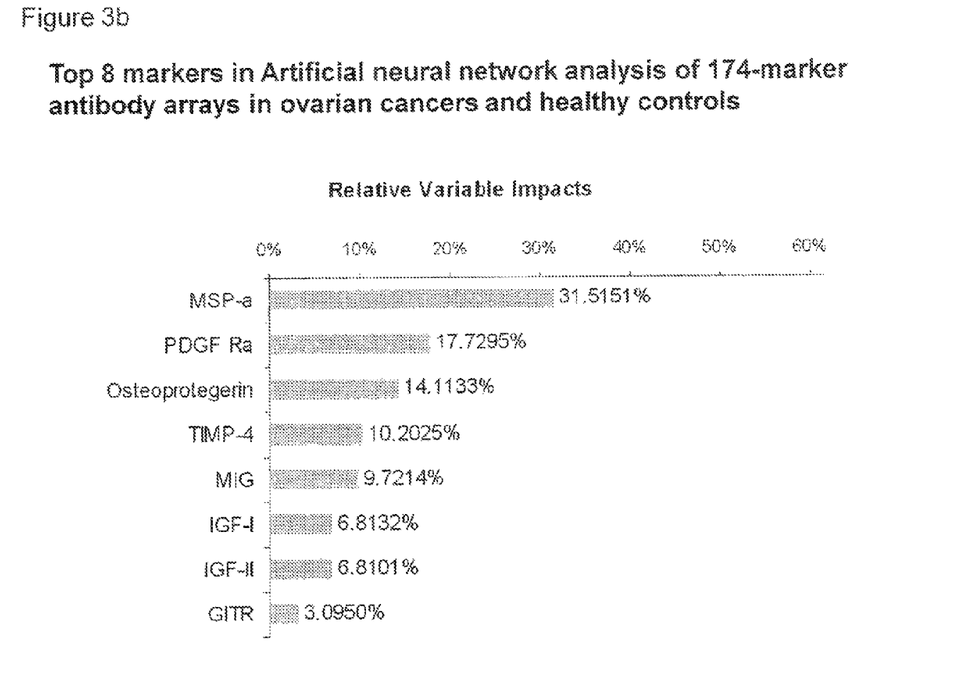

The data after normalization and filtration were then subjected to artificial neural network (ANN) analysis. The signal intensity data for individual patients were randomly divided into the training set (N=51) or prediction set (N=36). In prediction discovery phase, the training set was analyzed using leave-one cross-validation approach. Through this analysis, a total of 8 predictors were identified. These 8 predictors were then used to predict the disease status in the prediction set. The correct agreement with clinical diagnosis in the training set and the prediction set was 82% and 80% respectively. See FIG. 3.

Figure 4:
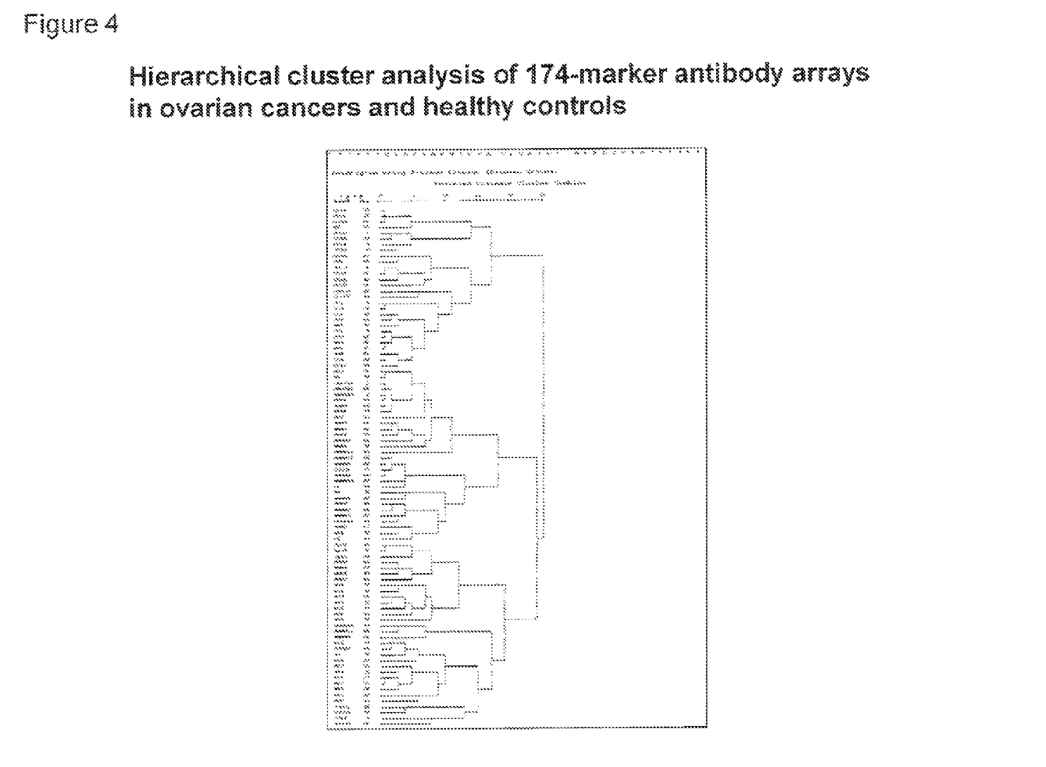
FIG. 4 shows a hierarchical cluster analysis of 174-marker antibody arrays in ovarian cancers and healthy controls.
Figure 5:
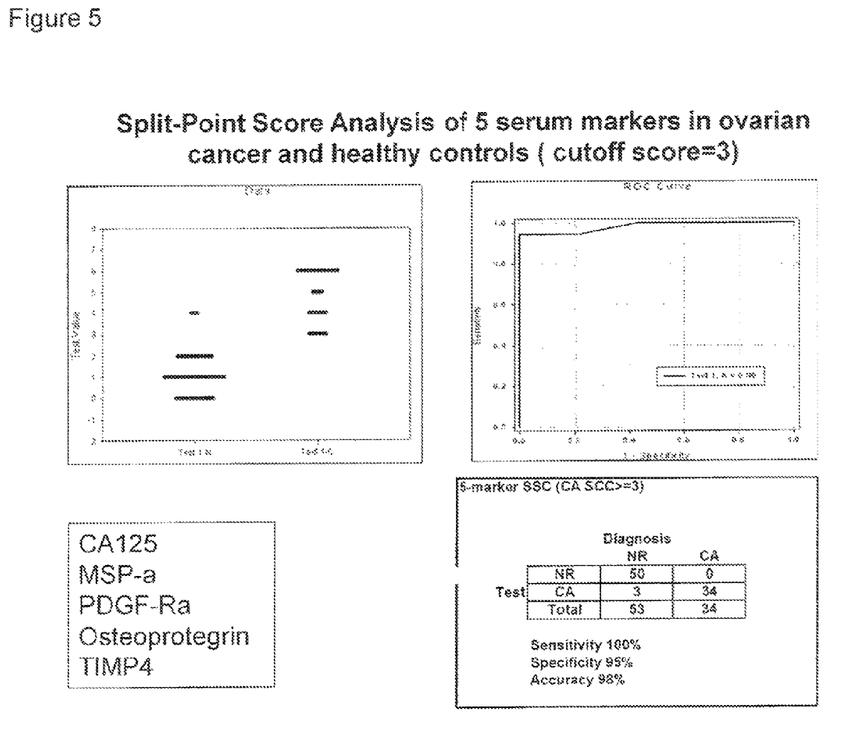
FIG. 5 shows Split-Point Score Analysis of 5 serum markers in ovarian cancer and healthy controls, wherein Panel A (top left) is a dot histogram plot with five-analyte split-point score classification of sera from healthy control (N) and ovarian cancer (CA), wherein correctly classified normal serum samples have a score of 0 to 2, whereas samples from ovarian cancer patients have a score of 3-5; Panel B (top right) is a ROC curve for 5 marker panel of split-score analysis of ovarian cancer vs. healthy controls, wherein the ROC is the curve plotted of sensitivity (true positive) against 1-specificity (false positive) values; and Panel C (bottom right) is a table using five-marker split-point score to classify ovarian cancer patients, using a cut-off score of 3.

Identification of 5-Marker Panel for Detection of Ovarian Cancer (FIGS. 4 and 5)

Next, we chose 4 of the 8 markers for hierarchal cluster analysis using SPSS software. 83% of samples have been correctly identified (95% of healthy controls and 62% of ovarian cancers).

Finally, all 87 samples were analyzed by the above-identified 4 serum markers plus CA125 using split-point score analysis. Using the cutoff score of 3, 100% ovarian cancer and 95% healthy control samples were correctly identified, giving the total correct agreement of 96.6%.

Since CA-125 is the most widely used marker for ovarian cancer, we compared the AUC between CA-125 and our 5-marker panel as determined by ROC curves. CA-125 alone had an AUC of 0.87. On the other hand, the 5-marker panel of the present invention had a AUC of 0.98. Thus, the present study shows a set of 5 serum markers for early detection of ovarian cancer.

Validation of 5-Marker Panel for Detection of Ovarian Cancer with ELISA Assay

Figure 6:
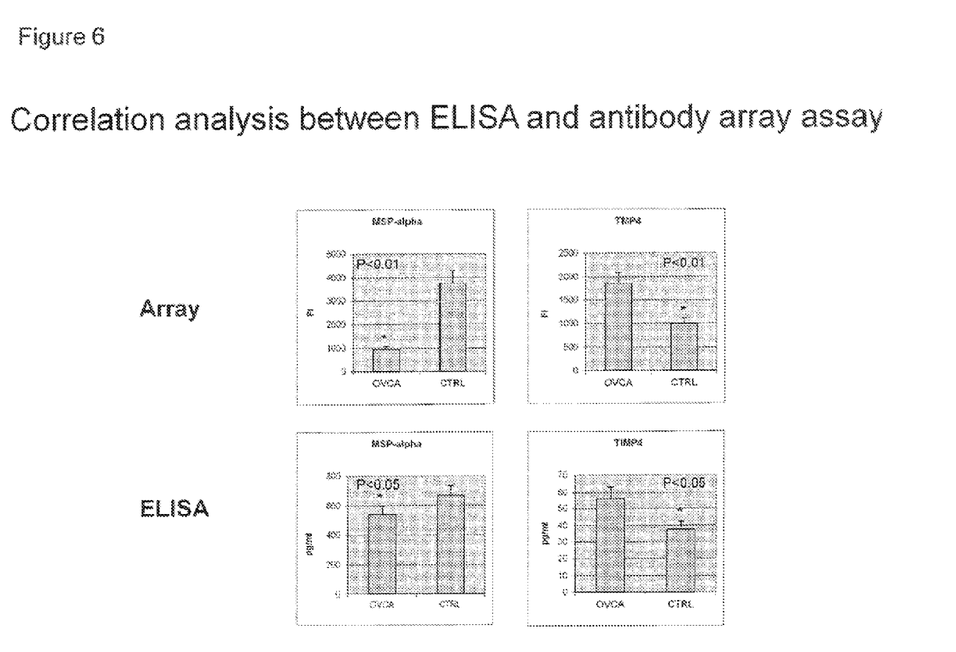
FIG. 6 shows a correlation analysis between ELISA and antibody array assays, wherein two protein markers (MSP-α and TIMP-4) identified with antibody array data and ELISA data were found to be completely concordant in classifying sera from ovarian cancer and healthy control, and wherein antibody array data are shown as median array signal intensity (FI) and ELISA data are shown as mean protein concentration (ng/ml).

All these 4 markers, including MSP-α, TIMP-4, PDGF-Rα, and OPG, identified by ANN analysis and split-point score analysis were confirmed by ELISA kits. FIG. 6 shows the representative data for two markers, MSP-α and TIMP-4.

All patent publications and non-patent publications are indicative of the level of skill of those skilled in the art to which this invention pertains. All these publications are herein incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An antibody array for the detection of ovarian cancer in a human or animal subject, comprising a solid support having disposed thereon in a predetermined spatial configuration, a panel of antibodies specific to biomarkers comprising CA-125, MSP-α, TIMP-4, PDGF-Rα and OPG, wherein the panel comprises a first antibody or fragment thereof that specifically binds CA-125, a second antibody or fragment thereof that specifically binds MSP-α, a third antibody or fragment thereof that specifically binds TIMP-4, a fourth antibody or fragment thereof that specifically binds PDGF-Rα, and a fifth antibody or fragment thereof that specifically binds OPG.

2. The antibody array of claim 1, wherein the antibodies are monoclonal antibodies.

3. The antibody array of claim 1, wherein the solid support comprises glass.

* * * * *